United States Patent [19]

Shalub et al.

[11] Patent Number: 5,962,147
[45] Date of Patent: Oct. 5, 1999

[54] METHOD OF BONDING WITH A NATURAL RUBBER LATEX AND LAMINATE PRODUCED

[75] Inventors: George J. Shalub, Languna Hills; Gregory Bellinger, Manifee; John Jackson, La Habra, all of Calif.

[73] Assignee: General Latex and Chemical Corporation, Cambridge, Mass.

[21] Appl. No.: 08/977,282

[22] Filed: Nov. 24, 1997

Related U.S. Application Data

[60] Provisional application No. 60/031,838, Nov. 26, 1996.
[51] Int. Cl.⁶ ..................................................... B32B 25/04
[52] U.S. Cl. .......................... 428/492; 428/440; 428/465
[58] Field of Search ............................ 524/493; 428/440, 428/465, 492

[56] References Cited

U.S. PATENT DOCUMENTS

| | | |
|---|---|---|
| 1,673,672 | 5/1928 | Gibbons et al. . |
| 1,829,992 | 11/1931 | Kemp . |
| 1,834,481 | 12/1931 | Vogel et al. . |
| 2,097,481 | 11/1937 | Wallerstein . |
| 2,116,089 | 5/1938 | Wallerstein . |
| 2,188,468 | 1/1940 | Albion . |
| 2,587,278 | 2/1952 | Bevilacqua . |
| 2,932,678 | 4/1960 | Seraran et al. . |
| 3,100,235 | 8/1963 | Graham et al. . |
| 4,194,995 | 3/1980 | Schermann ................................ 260/14 |
| 4,233,357 | 11/1980 | Taylor .................................... 428/245 |
| 4,379,095 | 4/1983 | Oldack .................................... 523/335 |
| 4,455,265 | 6/1984 | Haldeman . |
| 4,507,357 | 3/1985 | Lester ..................................... 428/278 |
| 4,549,897 | 10/1985 | Seng . |
| 4,638,028 | 1/1987 | Lui et al. . |
| 4,675,347 | 6/1987 | Mochizuki et al. . |
| 5,569,740 | 10/1996 | Tanaka .................................... 528/502 |
| 5,654,063 | 8/1997 | Kirk ......................................... 428/77 |

FOREIGN PATENT DOCUMENTS 6256404  1/1993  Japan .

*Primary Examiner*—Paul R. Michl
*Attorney, Agent, or Firm*—Richard P. Crowley

[57] ABSTRACT

A composition, system and method of bonding together two substrates employing a deproteinized, enzyme-treated, natural rubber latex composition as a contact curing adhesive between the substrate surfaces.

24 Claims, No Drawings

METHOD OF BONDING WITH A NATURAL RUBBER LATEX AND LAMINATE PRODUCED

REFERENCE TO PRIOR APPLICATIONS

This application claims the benefit of U.S. Provisional Application No. 60/031,838 filed Nov. 26, 1996, hereby incorporated by reference, and the benefit of which filing date is requested.

BACKGROUND OF THE INVENTION

Natural rubber latices derived from rubber trees are typically collected and processed into a preserved and stabilized latex composition for storage and shipment and usually contain about 60–62 percent by weight of natural rubber. Natural rubber latices are compounded and then used, for example, in the production of medical balloons, medical-examination gloves, catheters, breather bags, condoms, etc.

It is known that natural rubber latex contains small amounts of allergy-inducing proteins. A variety of enzymes have been used in natural rubber latex, to deproteinize the latex by the structural breakdown of the enzymes (usually hydrolysis to reduce or eliminate the allergy-inducing protein content). Proteolysis may be accomplished by the addition of various enzymes, such as trypsin, pepsin, rennin, and protease, to the natural rubber latex. The rate of hydrolysis of the proteins to the water-soluble peptide breakdown products is influenced by time, temperature, pH, and the presence of metallic ions and other substrates. The enzymes may be used in raw rubber latex, prevulcanized latex or finished compounded latex. Desensitized latices are required, where the natural rubber latex products come in contact with the human body. Adhesive products have been developed employing natural rubber latices, which generally include tackifiers, gelling agents, antioxidants, and surfactants.

It is desirable to provide a new and improved latex adhesive composition and method of bonding with enhanced contact bond strength and bonded systems and methods of bonding various materials employing such adhesive compositions.

SUMMARY OF THE INVENTION

The invention relates to enzyme-desensitized natural rubber latex contact adhesive compositions, to laminate systems employing the adhesive compositions as a bonding agent, and to the method of bonding such systems.

It has been unexpectedly discovered that natural rubber latex compositions treated with enzymes provide excellent contact adhesives between a wide variety of surfaces, to include, but not be limited to: foam-to-foam; primary and secondary backing for carpets, like mesh and nonwoven and woven sheets; solid rubber or leather to woven sheet material, like canvas, for use in footwear production; and in forming bead rolls in medical products, such as condoms, bags, and surgical gloves.

The adhesive natural rubber latex compositions useful as contact adhesives for substrates comprise a natural rubber latex composition which has been treated with one or more enzymes, alone or in combination or in sequence, to deproteinize the protein of the latex, typically by adding the enzyme to the natural rubber latex at general ambient temperatures for a selected period of time, usually 6 to 48 hours, but generally 24 or more hours. One or more stabilizers are added usually with the enzyme to an amount sufficient to stabilize the latex for use as an adhesive for a selected time period.

Normally, natural rubber latex compositions have an ASTM-tested, mechanical stabilization of about 450 to 500 seconds on receipt from a supplier. Such latex compositions typically are destabilized by the enzyme treatment to less than about 200 seconds in a 24-to-48-hour enzyme treatment. Where the natural rubber latex is used for a dipping operation, such as deproteinized medical gloves, then sufficient stabilizer is added, to provide an 800-seconds-plus-mechanism stabilization. In the present invention, the amount of stabilizer is much reduced, to provide a natural rubber latex composition with only a mechanical stability of less than about 200 to 300 seconds, so that the latex composition performs an adhesive contact composition and provides a good contact bond in less than about 1 to 2 minutes, and usually less than 20 to 40 seconds, for good bond strength.

Thus sufficient stabilizer must be employed, in a compromise fashion, after or with the enzyme treatment, to provide sufficient mechanical stability to permit handling and shipping of the composition and stability prior to use as an adhesive; for example, 1 to 4 weeks after receipt by a user, but not sufficient to affect the adhesive and bond strength of the composition, like the high stability required in a latex-glove dipping operation.

The latex-treated natural rubber enzyme usually will have some residual traces of the enzyme or its products in the composition. Therefore, further treatment or the addition of other enzymes, to remove such residue traces, may be carried out to improve the adhesive strength, and to control the final and desirable stability of the compounds.

The stabilizers employed for the adhesive latex composition are the usual stabilizers employed in mechanical stabilization of natural rubber latex compositions to prevent coagulation of the latex, but are employed in amounts of generally less than 0.5 parts of stabilizer per 100 parts of dry rubber solids; for example, 0.05 to 0.3 parts. Typical stabilizers would include, but not be limited to, long chain fatty acids and sulfonated fatty acids, anionic and nonionic surfactants, such as alkylphenol polyethoxylated surfactants and polyethoxylated fatty alcohols, and combinations thereof.

Thus the adhesive natural rubber latex compositions useful as contact adhesives comprise deproteinized, enzyme-treated (6 to 48 hours) natural rubber latex compositions having an ASTM D-1076-88 stability of about 200 to 400 seconds or less, and having a sufficient amount of a stabilizer to provide mechanical stability of up to one month prior to use, and a direct contact bond developing in less than 2 minutes, and generally in 10 to 60 seconds, after application and contact of the substrates.

The adhesive natural rubber latex compositions at 300 to 400 seconds or less are unstable, so that the use of low-shear, low-agitation techniques, such as the use of gravity-feed systems, are suggested for applications of the composition to the substrate surface. Where an adhesive composition is subject to continuous agitation or handling, the stability should be increased to 600 to 800+ seconds; however, the contact adhesive or bonding time is increased with some compositions. Where very fast-like solvent contact adhesive bonding is required; for example, less than 10 seconds, very low stability compositions are suggested.

The adhesive composition is applied to one or both surfaces of the substrates to be bonded, and the coated substrates then placed in contact with each other with a slight amount of pressure.

The natural rubber latex adhesive composition comprises a natural rubber latex, generally, but not limited to, over 60 percent; for example, about 60 to 62 percent, by weight, to which has been added one or more enzymes for proteolysis purposes; for example, 0.01 to 1.0 weight percent or more; for example, 0.05 to 0.5 weight percent, and then admixed generally at selected temperatures; for example, 15 to 25 C, for an enzyme reaction time of, for example, 6 to 48 hours. The natural rubber latex adhesive composition generally contains a stabilizing amount of a stabilizer, to overcome the instability of the latex to the enzyme addition, and is adjusted in pH to a pH usually of greater than 9.0; for example, 10 to 10.5. One stabilizer suitable for use would include a water-soluble alkali, such as potassium or sodium hydroxide, for example, in an amount of 0.05 to 2.00 weight percent. The adhesive composition also generally includes one or more curing agents and accelerators, to provide for the cure of the natural rubber latex either at ambient drying temperatures or in constant oven; for example, 260 to 285° F., or moving oven; for example, 325 to 350° F., curing operations. It is recognized that the natural rubber enzyme adhesive latex may include other additives and various combinations thereof, such as other stabilizers, detergents (anionic and nonionic), dispersants, accelerators, curing agents, thickeners, antioxidants, viscosity index improvers, tackifiers, and silicones, as well as fillers and pigments like metal sulfates, carbonates, and oxides.

An enhanced bond strength and fast-setting latex adhesive composition suitable to be sprayed on bonding surfaces; for example, at an angle of 90 degrees, may be prepared employing viscosity index improver additives, to control the viscosity, improve set time and improve adhesive bond strength. The increase in viscosity of the composition reduces penetration of the adhesive composition into the substrate; that is, a porous substrate like a foam, fabric, leather, paper and laminates and multiple laminates thereof, and makes the layer of adhesive composition ride higher on the surface, to improve bond strength. It has been found that the addition of silica particles, particularly aqueous dispersions of pyrogenic silica, and the use of silicate like alkali silicates, such as sodium silicate, in the amount of about 0.1 to 5.0 percent by weight, such as 0.5 to 3.0 percent, are useful to improve bond strength and increase viscosity to up to about 500 or more cps at 25° C., such as 50 to 350 cps.

The adhesive composition may be applied to one or both surfaces to be bonded, typically as a thin coating layer; for example, 0.5 to 10 mils, such as by spraying, dipping, rolling, coating, etc. Bonding of the surfaces occurs on drying, and a strong cured bond is developed. The bonding systems would comprise the use of open or closed-cell foam materials like urethane, olefinic rubber, and vinyl foam materials, as well as leather, metal and fabrics in various lamination arrangements. In particular, bonded laminates of urethane foams (polyether and polyester), natural rubber latex foams and foam-metal laminates, such as polyurethane foam to metals like aluminum, stainless steel, etc., may be prepared with the adhesive compositions.

The invention will be described for the purposes of illustration only in connection with certain preferred embodiments; however, it is recognized that those persons skilled in the art may make various modifications, changes, improvements, and additions to the illustrated embodiments without departing from the spirit and scope of the invention.

DESCRIPTION OF THE EMBODIMENTS

EXAMPLE 1

The adhesive latex was used as a carpet-repair composition, with a rubber accelerator-curing system and a pigment for securing a mesh material (Action-bac) onto the back surface of a tufted carpet. For example, often carboxylated styrene butadiene rubber (SBR) latex is used on the back surface of a carpet, but may not form a sufficiently strong bond, particularly in designer carpets, where an additional backing, like cotton cloth, is desired for cosmetic-aesthetic purposes. The adhesive latex may be used to secure secondary backings to the SBR-backed carpets.

EXAMPLE 2

The enzyme-containing adhesive latex composition was used in place of or to supplement solvent cements used, to provide rollup cuffs on latex products, like gloves, since the enzyme natural rubber adhesive latex will form a strong bond on rolling up of the cuffs after the leaching step, so that the bonded rollup cuff glove may then be sent to the oven for cure and then stripped from the form.

The initial use of enzymes in natural latex was to deproteinize the latex, thereby reducing human sensitivity to the proteins. It was observed that the enzymes destabilized and sensitized the compounds. To overcome the instability of the latex to enzyme addition, the stabilizers were drastically increased. Yet, with the extra stabilizers in the latex compound, the surface tack was not destroyed. This phenomenon was observed during leaching. If two glass tubes with natural rubber latex film came in contact, the glass tubes could easily be separated. This was not the case observed with the enzyme natural rubber latex. The tubes stuck and could not be separated.

EXAMPLE 3

Contact adhesive applications, especially in foam-to-foam adhesion, were carried out. Straight natural latex was used and an enzyme added. Foam pads were sprayed with the natural rubber latex with and without the enzyme. Approximately 30 seconds later, the two sprayed surfaces were stuck together. The enzyme natural rubber latex developed a strong bond, the natural latex did not. A carpet-repair compound was evaluated, which is, in itself, pressure-sensitive, again with and without enzyme. Once again, the bond was much stronger and surface tack was greater with the enzyme addition. Whenever the enzyme was added, the mechanical stability decreased and surface tack increased, due to the sensitizing of the latex compound by the enzyme. The enzyme level was reduced by 50% without sacrifice in surface tack. The following commercial enzymes are suitable latex sensitizers for the natural rubber adhesive compositions of the invention:

Alkaline Protease AP

Alkaline Protease AP R5800

Alkaline Protease AP solution #1 & #2

K-Zyme AP-400-S liquid.

EXAMPLE 4

Some further applications of the enzyme (protease), treated and desensitized, stabilized curable natural latex compounds with formulations as listed below, were prepared and tested as adhesive contact compositions:

Foam Adhesive: Both surfaces were sprayed and, within 15 seconds, the two sprayed surfaces were laminated. Two compounds are recommended:

| Compound A: | Natural latex | 167.00 |
| --- | --- | --- |
| | Potassium hydroxide solution | 1.00 |
| | Enzyme solution | 0.05–0.125 |
| Compound B: | Natural latex | 167.00 |
| | Potassium hydroxide | 0.20 |
| | Polyoxyethylated fatty alcohol | 2.00 |
| | Zinc dibenzyldithiocarbamate dispersion | 1.00 |
| | Sulfur dispersion | 1.00 |
| | Zinc oxide dispersion | 3.00 |
| | Antioxidant dispersion | 2.00 |
| | Enzyme (24–48 hours) | 0.08–0.125 |

Carpet-Repair Compound: For a strong bond with quick set, the carpet was sprayed and a carpet mesh material (Actionbac) pressed on the sprayed back. Within minutes, the carpet was rolled up.

| Natural latex | 167.00 |
| --- | --- |
| Potassium hydroxide | 0.20 |
| Sulfonated fatty products - anionic | 0.50 |
| Polyoxyethylated fatty alcohol - nonanionic | 1.00 |
| Zinc dibenzyldithiocarbamate dispersion | 2.00 |
| Sulfur dispersion | 2.00 |
| Zinc oxide dispersion | 6.00 |
| Antioxidant dispersion | 2.00 |
| Titanium dioxide dispersion | 4.00 |
| Enzyme (stability less than 300 seconds) | 0.08–0.125 |

Foxing Cement: To improve adhesion of a rubber strip to canvas or leather uppers.

| Natural latex | 167.00 |
| --- | --- |
| Potassium hydroxide solution | 3.00 |
| Zinc metcaptobenzothiziole dispersion | 1.50 |
| Sodium napthalene sulfonic acid salt | 6.00 |
| Antioxidant dispersion | 2.00 |
| Sulfur dispersion | 2.00 |
| Sodium carboxylic acid salt | 1.00 |
| Caseinate | 6.00 |
| Enzyme (stability less than 400 seconds) | 0.125–0.25 |
| Gloves: For strong bead rolls. | |
| Natural latex | 167.00 |
| Potassium hydroxide solution | 5.00 |
| Sodium alkylnapthylene sulfonate | 6.00 |
| Zinc metcaptobenzothiziole dispersion | 1.00 |
| Zinc dibutyldithiocarbamate | 1.00 |
| Sulfur dispersion | 2.00 |
| Zinc oxide dispersion | 6.00 |
| Enzyme (stability 800+ seconds) | 0.125–0.25 |

Adhesive latex compositions used for glove bead rolls are usually under substantially continuous mixing and agitating, and thus stabilities of 800+ seconds are required.

EXAMPLE 5

Suitable latex foam adhesive formulations are as follows:

| Natural latex | 167.00 |
| --- | --- |
| Zinc dibenzyldithiocarbamate | 4.00 |
| Sodium silicate or Cab-o-Sperse solution | 1.00–4.00 |
| Enzyme (24-hour treatment - stability less than 200 seconds) | 0.1–0.25 |
| Natural latex | 167.00 |
| Potassium hydroxide | 1.00 |
| Sulfonated fatty products - anionic | 0.5–2.0 |
| Zinc dibenzyldithiocarbamate | 4.00 |
| Sodium silicate N or Cab-o-Sperse | 1.0–4.0 |
| Enzyme (24–48-hour treatment - stability 200 to 300 seconds) | 0.1–0.25 |

These formulations containing viscosity index improvers of silica and silicates provide strong bonds, particularly in foam—foam laminates.

What is claimed is:

1. A method of bonding two substrates together, which method comprises:
   a) applying to one or both surfaces of the substrate a stabilized enzyme-treated, deproteinized, adhesive natural rubber latex composition;
   b) contacting and bonding the surfaces together; and
   c) recovering the latex bonded substrates.

2. The method of claim 1 wherein the latex composition comprises a natural rubber latex composition of over about 60 percent solids of natural rubber.

3. The method of claim 1 wherein the latex composition has been treated with an enzyme for proteolysis in an amount of about 0.01 to 1.0 weight percent of the composition.

4. The method of claim 1 wherein the latex composition includes from about 0.1 to 5.0 weight percent of the composition of silica or silicates, to increase the viscosity of the composition.

5. The method of claim 1 wherein one of the substrates is selected from the group consisting of canvas, rubber, foam, leather, metal, and a carpet-backing material.

6. The method of claim 1 wherein the substrates both are polymeric foam substrates.

7. The method of claim 1 wherein the latex composition includes a curing accelerator agent.

8. The method of claim 1 wherein the composition has a stability of less than about 400 seconds and bonds in less than about 2 minutes.

9. The method of claim 1 which includes applying the composition to the surface of the substrate by gravity feed of the composition.

10. The method of claim 1 wherein the composition includes a curing-accelerator agent, has a pH of greater than 9.0 and a stability of about 50 to 400 seconds.

11. The method of claim 1 wherein the viscosity ranges from about 50 to 350 cps.

12. The method of claim 1 wherein the latex composition provides a contact bond in about 5 minutes or less.

13. The latex bonded substrates produced by the method of claim 1.

14. A bonded laminate which comprises at least two substrates bonded together by an enzyme-treated, deproteinized, cured, natural rubber latex composition.

15. The method of claim 1 which includes bonding the surfaces together by heating and curing the natural rubber latex composition.

16. The method of claim 3 which includes treating the natural rubber latex composition having about 60 to 62 percent solids for a period of 6 to 48 hours at about 15–25° C.

17. The latex bonded substrate of claim 14 wherein the substrate includes a urethane foam or a natural rubber latex foam.

18. The method of claim 1 wherein one substrate includes a SBR latex backed, tufted carpet, and the other substrate is a secondary backing for the carpet.

19. The method of claim 1 wherein the substrates comprise a rolled up cuff on a latex glove.

20. The method of claim 1 wherein the substrates both comprise urethane foam substrates.

21. The method of claim 1 wherein the substrates comprise a rubber substrate and a canvas or leather shoe upper.

22. The method of claim 1 which includes applying the natural rubber latex composition by spraying one or both surfaces of the substrates.

23. The method of claim 1 which includes applying the natural rubber composition as a coating layer of about 0.5 to 10 mils in thickness.

24. The bonded laminate of claim 20 wherein the substrates includes at least one foam substrate.

* * * * *

UNITED STATES PATENT AND TRADEMARK OFFICE
CERTIFICATE OF CORRECTION

PATENT NO. : 5,962,147
DATED : October 5, 1999
INVENTOR(S) : George J. Shalhub

It is certified that error appears in the above-identified patent and that said Letters Patent is hereby corrected as shown below:

On the title page under item [19],

Delete "Shalub" and insert --Shalhub--.

On the title page item [75], the first listed inventor;

Delete "Shalub" and insert --Shalhub--.. Delete "Languna" and insert --Laguna--.

Column 8, claim 24, line 1, delete "claim 20" and insert --claim 14--.

Signed and Sealed this

Twenty-fifth Day of April, 2000

Attest:

Q. TODD DICKINSON

Attesting Officer

Director of Patents and Trademarks